(12) United States Patent
Ota et al.

(10) Patent No.: US 10,925,995 B2
(45) Date of Patent: Feb. 23, 2021

(54) ABSORBER AND ABSORBENT ARTICLE USING THE SAME

(71) Applicant: LIVEDO CORPORATION, Shikokuchuo (JP)

(72) Inventors: Yoshihisa Ota, Mima-gun (JP); Motoko Nishida, Mima-gun (JP); Masatoshi Ikeuchi, Mima-gun (JP)

(73) Assignee: LIVEDO CORPORATION, Shikokuchuo (JP)

( * ) Notice: Subject to any disclaimer, the term of this patent is extended or adjusted under 35 U.S.C. 154(b) by 1178 days.

(21) Appl. No.: 14/380,196

(22) PCT Filed: Feb. 20, 2013

(86) PCT No.: PCT/JP2013/000942
§ 371 (c)(1),
(2) Date: Aug. 21, 2014

(87) PCT Pub. No.: WO2013/125216
PCT Pub. Date: Aug. 29, 2013

(65) Prior Publication Data
US 2015/0024192 A1 Jan. 22, 2015

(30) Foreign Application Priority Data
Feb. 23, 2012 (JP) .............................. JP2012-038019

(51) Int. Cl.
*A61L 15/60* (2006.01)
*A61L 15/24* (2006.01)
*A61L 15/46* (2006.01)

(52) U.S. Cl.
CPC ............... *A61L 15/60* (2013.01); *A61L 15/24* (2013.01); *A61L 15/46* (2013.01); *A61L 2400/00* (2013.01); *Y10T 428/249991* (2015.04)

(58) Field of Classification Search
CPC .......... A61L 15/60; A61L 15/24; A61L 15/46; A61L 2400/00; Y10T 428/249991
(Continued)

(56) References Cited

U.S. PATENT DOCUMENTS 4,990,547 A * 2/1991 Stovicek ................. A01N 25/24
424/408
5,981,070 A * 11/1999 Ishizaki ................... A61L 15/60
428/403

(Continued)

FOREIGN PATENT DOCUMENTS

CN 1441813 A 9/2003
EP 1149593 A1 10/2001
(Continued)

*Primary Examiner* — Kelechi C Egwim
(74) *Attorney, Agent, or Firm* — Westerman, Hattori, Daniels & Adrian, LLP

(57) ABSTRACT

To provide an absorbent body and an absorbent article having excellent deodorization effect. The present invention provides an absorber comprising, a crosslinked polymer mainly composed of acrylic acid and having carboxyl groups thereof being at least partially neutralized as a water-absorbent resin powder, and an antibacterial cationic surfactant, wherein the antibacterial cationic surfactant is a compound neutralized with an acid having an acid dissociation constant pKa in water at 25 degrees centigrade in a range from 3.0 to 5.5.

12 Claims, 2 Drawing Sheets

(58) Field of Classification Search
USPC .......................................................... 524/560
See application file for complete search history.

(56) References Cited

U.S. PATENT DOCUMENTS

| | | | |
|---|---|---|---|
| 2003/0078349 A1 | 4/2003 | Tagawa et al. | |
| 2005/0209352 A1* | 9/2005 | Dairoku | A61L 15/60 521/50 |
| 2008/0221229 A1* | 9/2008 | Torii | A61F 13/53 521/56 |
| 2010/0240808 A1* | 9/2010 | Wada | B01J 20/261 524/78 |

FOREIGN PATENT DOCUMENTS

| | | | |
|---|---|---|---|
| JP | 09-248454 A | | 9/1997 |
| JP | 11-512944 A | | 11/1999 |
| JP | 2002-102280 A | | 4/2002 |
| JP | 2003-530967 A | | 2/2003 |
| JP | 2009-232685 A | | 10/2009 |
| JP | 2009232685 A | * | 10/2009 |
| WO | 97/46189 A1 | | 12/1997 |
| WO | 98/20916 A1 | | 5/1998 |
| WO | 99/38541 A1 | | 8/1999 |

* cited by examiner

[Fig. 1]
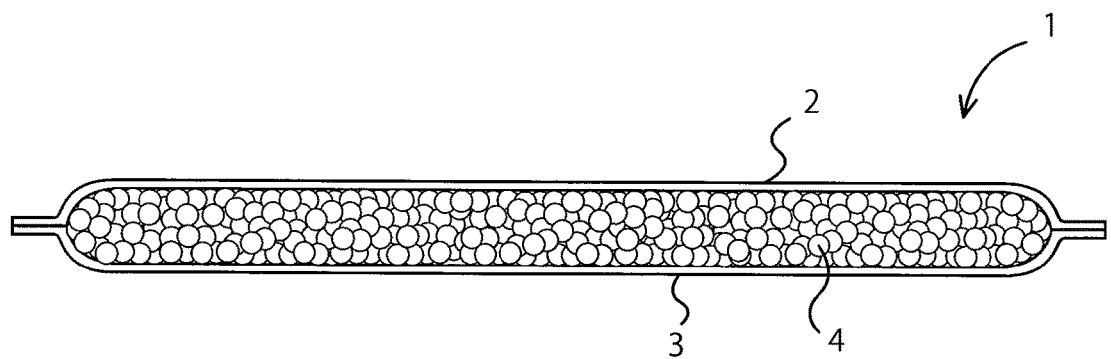
[Fig. 2]
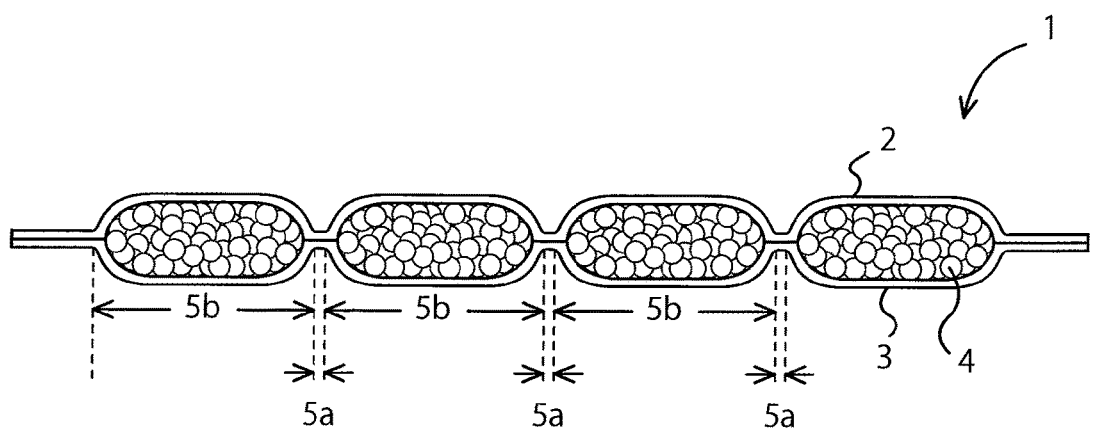
[Fig. 3]
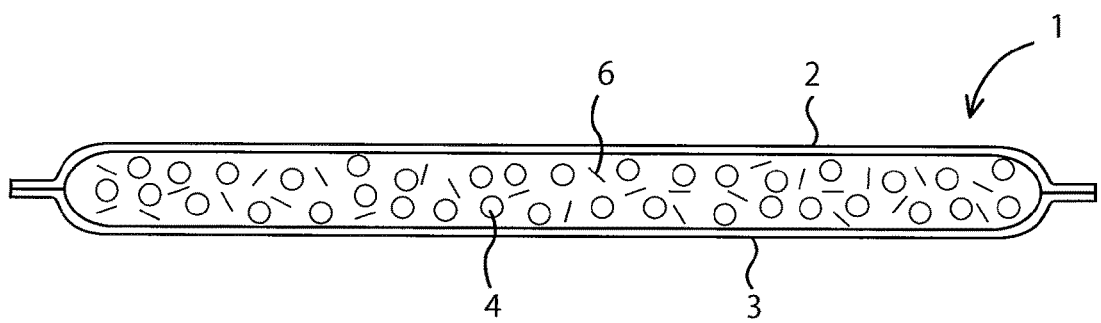

[Fig. 4]
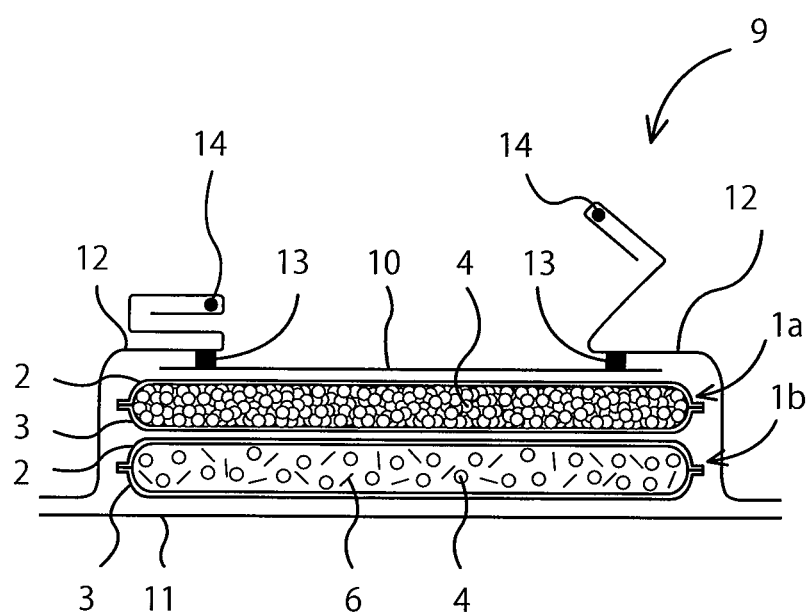

ABSORBER AND ABSORBENT ARTICLE USING THE SAME

TECHNICAL FIELD

The present invention relates to a technology for improving deodorization performance of absorbers and absorbent articles such as disposable diapers and sanitary napkins.

BACKGROUND ART

Absorbent articles such as diapers, sanitary napkins, and incontinence pads are used for absorbing and retaining body fluids such as urine and menstrual blood excreted from a human body. However, there is a demand for such absorbent articles to have a measure against unpleasant odors released while in use or when disposing of them after use.

For example, Patent Literature 1 discloses an absorbent product including a liquid-permeable top sheet, a back sheet, and an absorbent core interposed between the top sheet and the back sheet; wherein the absorbent product includes a deodorization system having a metallic silicate (excluding transition metals) or silica having a molecular weight of 136 or higher together with an absorbent gelling material. Patent Literature 2 discloses an absorbent article having at least one type of deodorizer selected from organic amines, organic amine salts, or substances that react with excrement, thereby generating organic amines. Patent Literature 3 discloses an absorbent article for pets including a liquid-permeable top sheet, a liquid-impermeable back sheet, and an absorber interposed therebetween; wherein the absorber includes (A) a fibrous absorber, (B) tea leaves and/or a tea-leaf extract, and (C) a surfactant having an antibacterial property.

CITATION LIST

Patent Literature

PTL 1: Japanese Patent Publication No. H11-512944
PTL 2: Japanese Patent Publication No. 2002-102280
PTL 3: Japanese Patent Publication No. 2009-232685

SUMMARY OF INVENTION

Technical Problem

As antibacterial agents, cationic surfactants are known. An absorber that has absorbed excrement such as urine will have a strong odor due to bacterial growth. Using an antibacterial cationic surfactant for an absorber should suppress bacterial growth and provide a deodorization effect. However, when an antibacterial cationic surfactant was used in an absorber, a problem occurred that the desired deodorization effect was not recognizable. The present invention has been made in view of the above circumstances, and an object of the present invention is to provide an absorber and an absorbent article having excellent deodorization effect.

Solution to Problem

The present inventors have achieved the present invention based on the findings that a sodium salt of a crosslinked polymer mainly composed of acrylic acid used as a water-absorbent resin affects the antibacterial cationic surfactant and lowers its deodorization function. More specifically, the antibacterial cationic surfactant applied to a water-absorbent resin exchanges its cationic component with the sodium salt of the crosslinked polymer, is trapped by the water-absorbent resin, and becomes less effective against bacteria. As a result, the deodorization effect is lowered.

The present invention, that has solved the above problem, provides an absorber comprising a crosslinked polymer mainly composed of acrylic acid and having carboxyl groups thereof being at least partially neutralized as a water-absorbent resin powder, and an antibacterial cationic surfactant, wherein the antibacterial cationic surfactant is a compound neutralized with an acid having an acid dissociation constant pKa in water at 25 degrees centigrade in a range from 3.0 to 5.5. The gist of the present invention resides in using a compound neutralized with an acid having an acid dissociation constant pKa in water at 25 degrees centigrade in a range from 3.0 to 5.5 as the antibacterial cationic surfactant. The acid dissociation constant in water at 25 degrees centigrade of acrylic acid, which is a main component of the crosslinked polymer, is 4.26. The antibacterial cationic surfactant neutralized with an acid having an acid dissociation constant close to that of acrylic acid, is unlikely to exchange cation with the water-absorbent resin powder. As a result, the antibacterial cationic surfactant used in the present invention is unlikely to be trapped by the water-absorbent resin and affects bacteria to exhibit its intrinsic deodorization effect.

The antibacterial cationic surfactant is preferably applied to at least a part of the water-absorbent resin powder. The deodorization effect can be enhanced by causing the antibacterial cationic surfactant to exist in or in the vicinity of the water-absorbent resin powder. The water-absorbent resin powder is preferably obtained by neutralizing at least a part of the carboxyl groups of the crosslinked polymer with a sodium ion. The absorber preferably comprises the antibacterial cationic surfactant in a content from 0.0005 mass % to 0.050 mass %.

The antibacterial cationic surfactant is more preferably a compound neutralized with an acid having an acid dissociation constant pKa in water at 25 degrees centigrade in a range from 3.18 to 5.24. The antibacterial cationic surfactant is preferably, for example, at least one compound selected from the group consisting of monoalkyl trimethyl ammonium salts, dialkyl dimethyl ammonium salts, monoalkyl monobenzyl dimethyl ammonium salts, and monoalkyl pyridinium salts.

For example, the absorber of the present invention may include a liquid-permeable first sheet, a second sheet, and an absorption layer comprising the water-absorbent resin powder disposed between the first sheet and the second sheet. The present invention includes an absorbent article having the absorber of the present invention.

Advantageous Effects of the Invention

The absorber and the absorbent article of the present invention have superior deodorization effect.

BRIEF DESCRIPTION OF DRAWINGS

FIG. 1 is a schematic sectional view of an absorber of a preferable embodiment of the present invention.
FIG. 2 is a schematic sectional view of an absorber of a preferable embodiment of the present invention.
FIG. 3 is a schematic sectional view of an absorber of a preferable embodiment of the present invention.
FIG. 4 is a schematic sectional view of an absorbent article of a preferable embodiment of the present invention.

DESCRIPTION OF EMBODIMENTS

The present invention is directed to an absorber comprising, a crosslinked polymer mainly composed of acrylic acid and having carboxyl groups thereof being at least partially neutralized as a water-absorbent resin powder, and an antibacterial cationic surfactant, wherein the antibacterial cationic surfactant is a compound neutralized with an acid having an acid dissociation constant pKa in water at 25 degrees centigrade in a range from 3.0 to 5.5.

First, the water-absorbent resin powder used in the present invention will be described. The water-absorbent resin powder used in the present invention is (A) a crosslinked polymer mainly composed of acrylic acid and having carboxyl groups thereof being at least partially neutralized. The content of the acrylic acid component constituting the crosslinked polymer is preferably 90 mass % or more, more preferably 95 mass % or more, and is preferably 99 mass % or less, more preferably 97 mass % or less. If the content of the acrylic acid component is within the above described range, the obtained water-absorbent resin powder can easily exhibit a desired absorption performance.

Examples of cations for neutralizing at least a part of the carboxyl groups of (A) the crosslinked polymer include, but not particularly limited to, alkali metal ions such as lithium, sodium, and potassium, and alkaline earth metal ions such as magnesium and calcium. Of those described above, at least a part of the carboxyl groups of the crosslinked polymer is preferably neutralized with the sodium ion. It should be noted that, with regard to neutralization of the carboxyl groups of the crosslinked polymer, neutralization may be conducted on the carboxyl groups of the crosslinked polymer which has been obtained by polymerization, or neutralization may be conducted in advance on a monomer which is then used for forming the crosslinked polymer.

The degree of neutralization of the carboxyl groups of the crosslinked polymer is preferably 60 mole % or more, and more preferably 65 mole % or more. This is because there are cases where the absorption performance of the obtained water-absorbent resin powder deteriorates if the degree of neutralization is too low. Furthermore, there is no particular limitation on the upper limit of the degree of neutralization, and all the carboxyl groups may be neutralized. It should be noted that the degree of neutralization is obtained by the following formula.

Degree of neutralization (mole %)=100×[Number of moles of neutralized carboxyl groups in the crosslinked polymer]/[Total number of moles of the carboxyl groups in the crosslinked polymer (including neutralized and unneutralized groups)], The crosslinked polymer (A) is preferably obtained by polymerizing an unsaturated monomer composition containing a water-soluble ethylenically unsaturated monomer (a1) and/or a hydrolyzable monomer (a2) producing the water-soluble ethylenically unsaturated monomer (a1) by hydrolysis; and an internal crosslinking agent (b).

The water-soluble ethylenically unsaturated monomer (a1) is not particularly limited, but a monomer having at least one water-soluble substituent and an ethylenically unsaturated group, or the like can be used. The water-soluble monomer means a monomer having a property of being dissolved at least in an amount of 100 g in 100 g of water at 25 degrees centigrade. In addition, the hydrolyzable monomer (a2) is hydrolyzed with water at 50 degrees centigrade, by the action of a catalyst (an acid, a base, or the like) where necessary, to produce the water-soluble ethylenically unsaturated monomer (a1). The hydrolysis of the hydrolyzable monomer (a2) may be conducted during or after the polymerization of the crosslinked polymer (A) or both during and after the polymerization of the crosslinked polymer (A). However, the hydrolysis of the hydrolyzable monomer (a2) is preferably conducted after the polymerization of the crosslinked polymer (A) in light of the molecular weight of the obtained water-absorbent resin powder and the like.

Examples of the water-soluble substituent include a carboxyl group, a sulfo group, a sulfoxy group, a phosphono group, a hydroxyl group, a carbamoyl group, an amino group, or salts thereof and an ammonium salt. A salt of a carboxyl group (a carboxylate), a salt of a sulfo group (a sulfonate), and an ammonium salt are preferred. In addition, examples of the salts include salts of alkali metal such as lithium, sodium, and potassium and salts of alkaline earth metal such as magnesium and calcium. The ammonium salt may be any of salts of primary to tertiary amines or a quaternary ammonium salt. Of these salts, in light of absorption properties, alkali metal salts and ammonium salts are preferred, and alkali metal salts are more preferred, and sodium salts are further preferred.

As the water-soluble ethylenically unsaturated monomer having a carboxyl group and/or a salt thereof, an unsaturated carboxylic acid having 3 to 30 carbon atoms and/or a salt thereof are preferred. Specific examples of the water-soluble ethylenically unsaturated monomer having a carboxyl group and/or a salt thereof include unsaturated monocarboxylic acids and/or salts thereof such as (meth)acrylic acid, (meth)acrylic acid salt, crotonic acid, and cinnamic acid; unsaturated dicarboxylic acids and/or salts thereof such as maleic acid, maleate, fumaric acid, citraconic acid, and itaconic acid; and monoalkyl (1 to 8 carbon atoms) esters of unsaturated dicarboxylic acids and/or salts thereof such as maleic acid monobutyl ester, fumaric acid monobutyl ester, ethylcarbitol monoester of maleic acid, ethylcarbitol monoester of fumaric acid, citraconic acid monobutyl ester, and itaconic acid glycol monoester. It is noted that in the description of the present invention, "(meth)acrylic" means "acrylic" and/or "methacrylic".

As a water-soluble ethylenically unsaturated monomer having a sulfo group and/or a salt thereof, a sulfonic acid having 2 to 30 carbon atoms and/or a slat thereof are preferred. Specific examples of the water-soluble ethylenically unsaturated monomer having a sulfo group and/or a salt thereof include aliphatic or aromatic vinyl sulfonic acids such as vinyl sulfonic acid, (meth)allyl sulfonic acid, styrene sulfonic acid, and alpha-methyl styrene sulfonic acid; (meth)acryloyl-containing alkyl sulfonic acids such as (meth)acryloxy propyl sulfonic acid, 2-hydroxy-3-(meth)acryloxy propyl sulfonic acid, 2-(meth)acryloylamino-2,2-dimethylethane sulfonic acid, 3-(meth)acryloxyethane sulfonic acid, 2-(meth)acrylamide-2-methylpropane sulfonic acid, and 3-(meth)acrylamide-2-hydroxypropane sulfonic acid; and alkyl(meth)allyl sulfosuccinate.

Examples of a water-soluble ethylenically unsaturated monomer having a sulfoxy group and/or a salt thereof include sulfate ester of hydroxyalkyl(meth)acrylate; and sulfate ester of polyoxyalkylene mono(meth)acrylate.

Examples of a water-soluble ethylenically unsaturated monomer having a phosphono group and/or a salt thereof include phosphate monoesters of (meth)acrylic acid hydroxyalkyl, phosphate diesters of (meth)acrylic acid hydroxyalkyl, and (meth)acrylic acid alkylphosphonic acids.

Examples of a water-soluble ethylenically unsaturated monomer having a hydroxyl group include mono-ethylenically unsaturated alcohols having 3 to 15 carbon atoms such as (meth)allyl alcohol and (meth)propenyl alcohol; mono-ethylenically unsaturated carboxylates or mono-ethylenically unsaturated ethers of bivalent to hexavalent polyols such as alkylene glycol having 2 to 20 carbon atoms, glycerin, sorbitan, diglycerin, pentaerythritol, and polyalkylene (2 to 4 carbon atoms) glycol (weight average molecular weight: 100 to 2000). Specific examples of them include hydroxyethyl(meth)acrylate, hydroxypropyl(meth)acrylate, tri-ethyleneglycol(meth)acrylate, and poly-oxyethylene-oxypropylene mono(meth)allyl ether.

Examples of a water-soluble ethylenically unsaturated monomer having a carbamoyl group include (meth)acrylamide; N-alkyl (1 to 8 carbon atoms) (meth)acrylamides such as N-methyl acrylamide; N,N-dialkyl (alkyl having 1 to 8 carbon atoms) acrylamides such as N,N-dimethyl acrylamide and N,N-di-n- or i-propyl acrylamide; N-hydroxyalkyl (1 to 8 carbon atoms) (meth)acrylamides such as N-methylol(meth)acrylamide and N-hydroxyethyl(meth)acrylamide; and N,N-dihydroxyalkyl (1 to 8 carbon atoms) (meth)acrylamides such as N,N-dihydroxyethyl(meth)acrylamide. As an unsaturated monomer having a group composed of an amide, in addition to them, vinyl lactams having 5 to 10 carbon atoms (N-vinyl pyrrolidone, etc.) and the like can also be used.

Examples of a water-soluble ethylenically unsaturated monomer having an amino group include an amino group-containing ester of a mono-ethylenically unsaturated mono- or di-carboxylic acid and an amino group-containing amide of a mono-ethylenically unsaturated mono- or di-carboxylic acid. As the amino group-containing ester of a mono-ethylenically unsaturated mono- or di-carboxylic acid, dialkylaminoalkyl(meth)acrylate, di(hydroxyalkyl)aminoalkyl ester, morpholinoalkyl ester, and the like can be used, and examples thereof include dimethylaminoethyl(meth)acrylate, diethylamino(meth)acrylate, morpholinoethyl(meth)acrylate, dimethylaminoethyl fumarate, and dimethylaminoethyl malate. As the amino group-containing amide of a mono-ethylenically unsaturated mono- or di-carboxylic acid, monoalkyl(meth)acrylamide is preferred, and examples thereof include dimethylaminoethyl(meth)acrylamide and diethylaminoethyl(meth)acrylamide. As the water-soluble ethylenically unsaturated monomer having an amino group, in addition to them, vinylpyridines such as 4-vinylpyridine and 2-vinylpyridine can also be used.

The hydrolyzable monomer (a2) producing the water-soluble ethylenically unsaturated monomer (a1) by hydrolysis is not particularly limited, but an ethylenically unsaturated monomer having at least one hydrolyzable substituent that becomes a water-soluble substituent by hydrolysis is preferred. Examples of the hydrolyzable substituent include a group containing an acid anhydride, a group containing an ester linkage, and a cyano group.

As an ethylenically unsaturated monomer having a group containing an acid anhydride, an unsaturated dicarboxylic anhydride having 4 to 20 carbon atoms is used, and examples thereof include maleic anhydride, itaconic anhydride, and citraconic anhydride. Examples of an ethylenically unsaturated monomer having a group containing an ester linkage include lower alkyl esters of mono-ethylenically unsaturated carboxylic acids such as methyl(meth)acrylate and ethyl(meth)acrylate; and esters of mono-ethylenically unsaturated alcohols such as vinyl acetate and (meth)allyl acetate. Examples of an ethylenically unsaturated monomer having a cyano group include vinyl group-containing nitrile compounds having 3 to 6 carbon atoms such as (meth)acrylonitrile and 5-hexenenitrile.

As the water-soluble ethylenically unsaturated monomer (a1) and the hydrolyzable monomer (a2), those described in Japanese Patent No. 3648553, Japanese Patent Publication No. 2003-165883, Japanese Patent Publication No. 2005-75982, and Japanese Patent Publication No. 2005-95759 can be further used. As each of the water-soluble ethylenically unsaturated monomer (a1) and the hydrolyzable monomer (a2), a single monomer or a mixture of two or more monomers may be used.

In addition to the water-soluble ethylenically unsaturated monomer (a1) and the hydrolyzable monomer (a2), another vinyl monomer (a3) that is copolymerizable with these monomers can be used for the unsaturated monomer composition. As the copolymerizable other vinyl monomer (a3), hydrophobic vinyl monomers and the like can be used, but it is not limited to them. As the other vinyl monomer (a3), the following vinyl monomers (i) to (iii) and the like are used.

(i) Aromatic ethylenically unsaturated monomers having 8 to 30 carbon atoms; Styrenes such as styrene, alpha-methylstyrene, vinyltoluene, and hydroxystyrene; vinylnaphthalene; and halogen substitutions of styrene such as dichlorostyrene.

(ii) Aliphatic ethylenically unsaturated monomers having 2 to 20 carbon atoms; Alkenes such as ethylene, propylene, butene, isobutylene, pentene, heptene, diisobutylene, octene, dodecene, and octadecene; and alkadienes such as butadiene, and isoprene.

(iii) Alicyclic ethylenically unsaturated monomers having 5 to 15 carbon atoms; Mono-ethylenically unsaturated monomers such as pinene, limonene, and indene; and poly-ethylenic vinyl-polymerizable monomers such as cyclopentadiene, bicyclopentadiene, and ethylidene norbornene.

As the other vinyl monomer (a3), those described in Japanese Patent No. 3648553, Japanese Publication No. 2003-165883, Japanese Patent Publication No. 2005-75982, and Japanese Patent Publication No. 2005-95759 can be further used.

From the aspect of providing the crosslinked polymer mainly composed of acrylic acid, as the water-soluble ethylenically unsaturated monomer (a1)) and/or the hydrolyzable monomer (a2) producing the water-soluble ethylenically unsaturated monomer (a1) by hydrolysis, acrylic acid or a salt of acrylic acid (a1), or a hydrolyzable monomer (a2) producing acrylic acid or the salt of acrylic acid is preferable. The content of acrylic acid or the salt of acrylic acid (a1), or the hydrolyzable monomer (a2) producing acrylic acid or the salt of acrylic acid in the unsaturated monomer composition constituting the crosslinked polymer is preferably 90 mass % or more, more preferably 95 mass % or more, and is preferably 99 mass % or less, more preferably 97 mass % or less.

Examples of the internal crosslinking agent (b) can include an internal crosslinking agent (b1) having two or more ethylenically unsaturated groups; an internal crosslinking agent (b2) having at least one functional group that can react with a water-soluble substituent of the water-soluble ethylenically unsaturated monomer (a1) and/or a water-soluble substituent produced by hydrolysis of the hydrolyzable monomer (a2) and at least one ethylenically unsaturated group; and an internal crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2).

Examples of the internal crosslinking agent (b1) having two or more ethylenically unsaturated groups include bis (meth)acrylamides having 8 to 12 carbon atoms, poly(meth)acrylates of polyols having 2 to 10 carbon atoms, polyallylamines having 2 to 10 carbon atoms, and poly(meth)allyl ethers of polyols having 2 to 10 carbon atoms. Specific examples of them include N,N'-methylene bis(meth)acrylamide, ethylene glycol di(meth)acrylate, poly(polymerization degree of 2 to 5) ethylene glycol di(meth)acrylate, propylene glycol di(meth)acrylate, glycerol(di or tri)acrylate, trimethylol propane triacrylate, diallylamine, triallylamine, triallylcyanurate, triallylisocyanurate, tetraallyloxyethane, pentaerythritol diallyl ether, pentaerythritol triallyl ether, pentaerythritol tetraallyl ether, and diglycerin di(meth)acrylate.

Examples of the internal crosslinking agent (b2) having at least one functional group that can react with a water-soluble substituent of the water-soluble ethylenically unsaturated monomer (a1)) and/or a water-soluble substituent produced by hydrolysis of the hydrolyzable monomer (a2) and at least one ethylenically unsaturated group include ethylenically unsaturated compounds having 6 to 8 carbon atoms and an epoxy group, ethylenically unsaturated compounds having 4 to 8 carbon atoms and a hydroxyl group, and ethylenically unsaturated compounds having 4 to 8 carbon atoms and an isocyanato group. Specific examples of them include glycidyl(meth)acrylate, N-methylol(meth)acrylamide, hydroxyethyl(meth)acrylate, and isocyanato ethyl(meth)acrylate.

Examples of the internal crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2) can include polyhydric alcohols, polyvalent glycidyls, polyvalent amines, polyvalent aziridines, and polyvalent isocyanates. Examples of polyvalent glycidyl compounds include ethylene glycol diglycidyl ether and glycerin diglycidyl ether. Examples of polyvalent amine compounds include ethylenediamine, diethylenetriamine, triethylenetetramine, tetraethylenepentamine, pentaethylenehexamine, and polyethyleneimine. Examples of polyvalent aziridine compounds include Chemitite PZ-33 {2,2-bishydroxymethylbutanol-tris(3-(1-aziridinyl)propionate)}, Chemitite HZ-22 {1,6-hexamethylenediethyleneurea}, and Chemitite DZ-22 {diphenylmethane-bis-4,4'-N,N'-diethyleneurea}, available from Nippon Shokubai Co., Ltd. Examples of polyvalent polyisocyanate compounds include 2,4-tolylene diisocyanate and hexamethylene diisocyanate. These internal crosslinking agents may be used singly or two or more of them may be used in combination.

As the internal crosslinking agent (b), in light of absorbing performance (in particular, an absorption amount, an absorption speed, etc.), the internal crosslinking agent (b1) having two or more ethylenically unsaturated groups is preferred, poly(meth)allyl ethers of polyols having 2 to 10 carbon atoms are more preferred, triallylcyanurate, triallylisocyanurate, tetraallyloxyethane, or pentaerythritol triallyl ether is further preferred, and pentaerythritol triallyl ether is most preferred.

As the internal crosslinking agent (b), those described in Japanese Patent No. 3648553, Japanese Patent Publication No. 2003-165883, Japanese Patent Publication No. 2005-75982, and Japanese Patent Publication No. 2005-95759 can be further used.

As the method for polymerizing the crosslinked polymer (A), a conventionally known method and the like can be used, and a solution polymerization method, an emulsion polymerization method, a suspension polymerization method, and a reversed-phase suspension polymerization method can be used. In addition, a polymerization liquid at the polymerization may be in the form of a thin film, mist, or the like. As the method for controlling the polymerization, an adiabatic polymerization method, a temperature-controlled polymerization method, an isothermal polymerization method, and the like can be used. As the polymerization method, the solution polymerization method is preferred, and an aqueous solution polymerization method is more preferred since an organic solvent and the like are not used and it is advantageous in terms of production cost.

A water-containing gel {consisting of the crosslinked polymer and water} obtained by the polymerization can be chopped where necessary. The size (largest diameter) of the chopped gel is preferably from 50 micrometers to 10 cm, more preferably from 100 micrometers to 2 cm, and even more preferably from 1 mm to 1 cm. If the size falls within this range, dryability at a drying process becomes further favorable.

The chopping can be conducted by a known method, and can be conducted, for example, by using a conventional chopping apparatus such as a Bexmill, a rubber chopper, a Pharma Mill, a mincing machine, an impact type mill, and a roll type mill.

When a solvent (an organic solvent, water, etc.) is used for the polymerization, it is preferred to remove the solvent by distillation after the polymerization. When the solvent contains water as a solvent, the water content (mass %) with respect to the mass (100 mass %) of the crosslinked polymer after the removal by distillation is preferably from 0 mass % to 20 mass %, more preferably from 1 mass % to 10 mass %, even more preferably from 2 mass % to 9 mass %, and most preferably from 3 mass % to 8 mass %. When the water content (% by mass) falls within the above range, the absorbing performance and the breakability of the water-absorbent resin powder after drying become further favorable.

It is noted that the content of the organic solvent and the water content are obtained based on a decrease in the mass of a measurement sample from before heating to after heating by an infrared moisture measuring instrument {JE400 manufactured by Kett Electric Laboratory or the like: 120 plus or minus 5 degrees centigrade, 30 minutes, an atmospheric humidity before heating of 50 plus or minus 10% RH, lamp specifications of 100 V and 40 W}.

As the method for removing the solvent (including water) by distillation, a method in which removal by distillation (drying) is conducted by hot air at a temperature in a range from 80 degrees centigrade to 230 degrees centigrade, a thin film drying method with a drum dryer or the like heated at the temperature in a range from 100 degrees centigrade to 230 degrees centigrade, a (heating) reduced-pressure drying method, a freeze-drying method, a drying method with infrared rays, decantation, filtration, and the like can be used.

The crosslinked polymer (A) can be pulverized after being dried. The pulverizing method is not particularly limited, and, for example, an ordinary pulverizing apparatus such as a hammer type pulverizer, an impact type pulverizer, a roll type pulverizer, and a jet streaming type pulverizer can be used. The particle size of the pulverized crosslinked polymer (A) can be adjusted by sieving or the like where necessary.

The weight average particle size (micrometer) of the crosslinked polymer (A) that is sieved where necessary is preferably from 100 micrometers to 800 micrometers, more preferably from 200 micrometers to 700 micrometers, even more preferably from 250 micrometers to 600 micrometers, particularly preferably from 300 micrometers to 500 micrometers, and most preferably from 350 micrometers to 450 micrometers. When the weight average particle size (micrometer) of the crosslinked polymer (A) falls within the above range, the absorbing performance becomes further favorable.

It is noted that the weight average particle size is measured with a ro-tap test sieve shaker and standard sieves (JIS Z8801-1: 2006) according to the method described in Perry's Chemical Engineers Handbook, Sixth Edition (The McGraw-Hill Companies, 1984, Page 21). In other words, as JIS standard sieves, for example, sieves of 1000 micrometers, 850 micrometers, 710 micrometers, 500 micrometers, 425 micrometers, 355 micrometers, 250 micrometers, 150 micrometers, 125 micrometers, 75 micrometers, and 45 micrometers, and a tray are combined in order from above. About 50 g of a measurement particle is placed into the uppermost sieve, and shaken with the ro-tap test sieve shaker for 5 minutes. The weights of the measurement particles on each sieve and the tray are measured, and the weight fraction of the particles on each sieve is obtained with the total weight regarded as 100% by weight. The values are plotted in a log probability paper {the horizontal axis is used for the opening of the sieve (particle size) and the vertical axis is used for the weight fraction}, then a line is drawn so as to connect each point, and a particle size corresponding to 50% by weight of the weight fraction is obtained and regarded as a weight average particle size.

The crosslinked polymer (A) may be treated with a surface modifier (B). Examples of the surface modifier (B) include polyvalent metal compounds such as aluminum sulfate, potassium alum, ammonium alum, sodium alum, (poly) aluminum chloride, and hydrates thereof; polycation compounds such as polyethyleneimine, polyvinylamine, and polyallylamine; inorganic fine particles; a surface modifier (B1) containing a hydrocarbon group; a surface modifier (B2) containing a hydrocarbon group having a fluorine atom; and a surface modifier (B3) having a polysiloxane structure.

Examples of the inorganic fine particles include oxides such as silicon oxide, aluminum oxide, iron oxide, titanium oxide, magnesium oxide, and zirconium oxide, carbides such as silicon carbide and aluminum carbide, nitrides such as titanium nitride, and complexes thereof (e.g., zeolite, talc, etc.). Among them, oxides are preferred, and silicon oxide is further preferred. The volume average particle size of the inorganic fine particles is preferably from 10 nm to 5000 nm, more preferably from 30 nm to 1000 nm, even more preferably from 50 nm to 750 nm, and most preferably from 90 nm to 500 nm. It is noted that the volume average particle size is measured in a solvent by a dynamic light scattering method. Specifically, the volume average particle size is measured in cyclohexane as a solvent at a temperature of 25 degrees centigrade by using the nano track particle size distribution measuring instrument UPA-EX150 (light source: He—Ne laser) manufactured by Nikkiso Co., Ltd.

Examples of the surface modifier (B1) containing a hydrocarbon group include polyolefin resins, polyolefin resin derivatives, polystyrene resins, polystyrene resin derivatives, waxes, long-chain fatty acid esters, long-chain fatty acids and salts thereof, long-chain aliphatic alcohols, and mixtures of two or more of them.

Examples of the surface modifier (B2) containing a hydrocarbon group having a fluorine atom include perfluoroalkanes, perfluoroalkenes, perfluoroaryls, perfluoroalkyl ethers, perfluoroalkylcarboxylic acids or salts thereof, perfluoroalkyl alcohols, and mixtures of two or more of them.

Examples of the surface modifier (B3) having a polysiloxane structure include polydimethylsiloxane; polyether-modified polysiloxanes such as polyoxyethylene-modified polysiloxane and poly(oxyethylene/oxypropylene)-modified polysiloxane; carboxy-modified polysiloxanes; epoxy-modified polysiloxanes; amino-modified polysiloxanes; alkoxy-modified polysiloxanes; and mixtures thereof.

As the surface modifier (B), in light of absorption properties, the surface modifier (B3) having a polysiloxane structure and inorganic fine particles are preferred, and amino-modified polysiloxanes, carboxy-modified polysiloxanes, and silica are more preferred.

The method for treating the crosslinked polymer (A) with the surface modifier (B) is not particularly limited, as long as treatment is conducted such that the surface modifier (B) is present on the surface of the crosslinked polymer (A). However, from the standpoint that the amount of the surface modifier (B) on the surface is controlled, it is preferred that the surface modifier (B) is mixed with a dried product of the crosslinked polymer (A), not with a water-containing gel of the crosslinked polymer (A) or a polymerization liquid that is prior to polymerization of the crosslinked polymer (A). It is noted that it is preferred that the mixing is uniformly conducted.

The shape of the water-absorbent resin powder is not particularly limited, and examples thereof include an indefinite crushed shape, a scale shape, a pearl shape, and a rice grain shape. Of them, the indefinite crushed shape is preferred from the standpoint that the powder in such a shape can be well entangled with fibrous materials in applications such as a disposable diaper and there is little possibility of the powder falling off from the fibrous materials.

The crosslinked polymer can be subjected to surface crosslinking where necessary. As a crosslinking agent for conducting the surface crosslinking (a surface crosslinking agent), the same ones as the internal crosslinking agent (b) can be used. In light of absorption performance and the like of the water-absorbent resin powder, the surface crosslinking agent is preferably the crosslinking agent (b3) having at least two functional groups that can react with a water-soluble substituent of the water-soluble ethylenically unsaturated monomer (a1) and/or a water-soluble substituent produced by hydrolysis of the hydrolyzable monomer (a2), more preferably a polyvalent glycidyl, even more preferably ethylene glycol diglycidyl ether and glycerin diglycidyl ether, and most preferably ethylene glycol diglycidyl ether.

In the case of conducting the surface crosslinking, the content (mass %) of the surface crosslinking agent with respect to the total mass (100 mass %) of the water-soluble ethylenically unsaturated monomer (a1) and/or the hydrolyzable monomer (a2), the internal crosslinking agent (b), and the other vinyl monomer (a3) used where necessary is preferably from 0.001 mass % to 7 mass %, more preferably from 0.002 mass % to 5 mass %, and even more preferably 0.003 mass % to 4 mass %. In other words, in this case, the upper limit of the content of the surface crosslinking agent based on the total mass of (a1) and/or (a2), (b), and (a3) is preferably 7 mass %, more preferably 5 mass %, and even more preferably 4 mass % by. Similarly, the lower limit is preferably 0.001 mass %, more preferably 0.002 mass %, and even more preferably 0.003 mass %. If the content of the surface crosslinking agent falls within the above range, the absorption performance becomes further favorable. The surface crosslinking can be achieved by, for example, a method of spraying an aqueous solution containing the surface crosslinking agent to the water-absorbent resin powder or impregnating the water-absorbent resin powder with the aqueous solution containing the surface crosslinking agent, followed by heating treatment (100 to 200 degrees centigrade) on the water-absorbent resin powder.

(2) Antibacterial Cationic Surfactant

The antibacterial cationic surfactant used in the present invention is not limited, as long as it is a cationic surfactant having the antibacterial property and is a compound neutralized with an acid having an acid dissociation constant pKa in water at 25 degrees centigrade in a range from 3.0 to 5.5. As the antibacterial cationic surfactant used in the present invention, for example, the cationic surfactant represented by the following formulae (1) to (3) which is a compound neutralized with an acid having an acid dissociation constant pKa in water at 25 degrees centigrade in a range from 3.0 to 5.5 can be preferably used.

[Chem. 1]

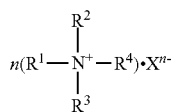
(1)

In formula (1), $R^1$, $R^2$, $R^3$, and $R^4$ are preferably each an identical or different hydrocarbon group having a carbon number of 1 to 22, and are more preferably each a linear- or branched-alkyl group or alkenyl group. In the formula, n is an integer of 1 to 4, and $X^{n-}$ is an n-valent anion of an acid. Specific examples thereof include the following <1> and <2>.

<1> $R^1$ and $R^2$ are each a linear or branched alkyl group having a carbon number of 8 to 12, and $R^3$ and $R^4$ are each an alkyl group having a carbon number of 1 to 3 (e.g., a dialkyl dimethyl ammonium salt).

<2> $R^1$ is a linear or branched alkyl group having a carbon number of 12 to 20; and $R^2$, $R^3$, and $R^4$ are each an alkyl group having a carbon number of 1 to 3 (e.g., a monoalkyl trimethyl ammonium salt).

Of <1> and <2>, <1> is preferable. More preferably in (1), $R^1$ and $R^2$ are each a decyl group and $R^3$ and $R^4$ are each a methyl group.

Specific examples of a quaternary ammonium group shown in formula (1) include the following.

<1> Octyl decyl dimethyl ammonium, dioctyl dimethyl ammonium, didecyl dimethyl ammonium, decyl dodecyl dimethyl ammonium, didodecyl dimethyl ammonium, octyl decyl methyl ethyl ammonium, dioctyl methyl ethyl ammonium, didecyl methyl ethyl ammonium, didodecyl methyl ethyl ammonium, didecyl methyl propyl ammonium, didodecyl ethyl propyl ammonium, etc.

<2> Dodecyl trimethyl ammonium, tetradecyl trimethyl ammonium, hexadecyl trimethyl ammonium, octadecyl trimethyl ammonium, dodecyl dimethyl ethyl ammonium, tetradecyl dimethyl ethyl ammonium, hexadecyl dimethyl ethyl ammonium, octadecyl dimethyl ethyl ammonium, dodecyl methyl diethyl ammonium, tetradecyl methyl diethyl ammonium, hexadecyl methyl diethyl ammonium, octadecyl methyl diethyl ammonium, etc. Of these, octyl decyl dimethyl ammonium, didecyl dimethyl ammonium, and decyl dodecyl dimethyl ammonium are preferable; and didecyl dimethyl ammonium is particularly preferable.

[Chem. 2]

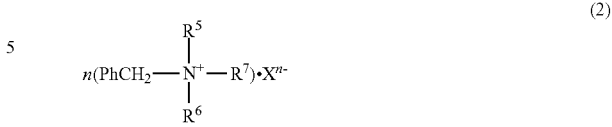
(2)

In formula (2), $R^5$, $R^6$, and $R^7$ are preferably each an identical or different hydrocarbon group having a carbon number of 1 to 22, and are more preferably each a linear- or branched-alkyl group or alkenyl group. In the formula, n is an integer of 1 to 4, and $X^{n-}$ is an n-valent anion of an acid. Preferably, $R^5$ is a linear or branched alkyl group having a carbon number of 8 to 18; and $R^6$ and $R^7$ are each an alkyl group having a carbon number of 1 to 3. More preferably, $R^5$ is a linear or branched alkyl group having a carbon number of 10 to 16; and $R^6$ and $R^7$ are each a methyl group (e.g., a monoalkyl monobenzyl dimethyl ammonium salt). In the formula, Ph is a phenyl group.

Specific examples of a quaternary ammonium group shown in formula (2) include decyl dimethyl benzyl ammonium, dodecyl dimethyl benzyl ammonium, tetradecyl dimethyl benzyl ammonium, hexadecyl dimethyl benzyl ammonium, coconut oil alkyl dimethyl benzyl ammonium, etc. Of those, dodecyl dimethyl benzyl ammonium and tetradecyl dimethyl benzyl ammonium are preferable.

[Chem. 3]

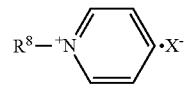
(3)

In formula (3), $R^8$ is preferably a hydrocarbon group having a carbon number of 5 to 20, more preferably a carbon number of 6 to 18; and even more preferably a linear- or branched-alkyl group or alkenyl group (e.g., a monoalkyl pyridinium salt). Specific examples of a pyridinium group represented in formula (3) include decyl pyridinium, dodecyl pyridinium, tetradecyl pyridinium, etc.

The antibacterial cationic surfactant used in the present invention is a compound neutralized with an acid having an acid dissociation constant pKa in water at 25 degrees centigrade in a range from 3.0 to 5.5. Specifically, an acid ($H_nX^{n-}$) having an anion (an n-valent anion of an acid represented by $X^{n-}$; n=1 to 4) of the antibacterial cationic surfactant represented by formulae (1) to (3) has an acid dissociation constant in water at 25 degrees centigrade in a range from 3.0 to 5.5. For example, an acid dissociation constant pKa of an acid ($H_n^{n-}$) is represented by the following formula.

pKa=−log(1/Ka), Ka=[$H^+$]$^n$x[$X^{n-}$]/[$H_nX^{n-}$]

For example, the antibacterial cationic surfactant used in the present invention can be produced in the following manner. An antibacterial cationic surfactant that is commonly commercially-available is a compound neutralized with a strong acid (e.g., hydrochloric acid-Cl, oxalic acid-Br). It is possible to obtain the antibacterial cationic surfactant of the present invention through a salt exchange reaction between a common antibacterial cationic surfactant neutralized with a strong acid and a neutralized salt compound formed from an acid having an acid dissociation constant pKa in water at 25 degrees centigrade in a range from 3.0 to 5.5 and a strong base (e.g., sodium hydroxide, potassium hydroxide). Although the salt exchange reaction can be conducted by mixing the both, it is possible to safely and easily allow the reaction to occur by agitating the mixture in a diluted condition with a solvent such as water, and, if necessary, heating the mixture (80 degrees centigrade to 95 degrees centigrade when water is used). By these reactions, the antibacterial cationic surfactant of the present invention is produced in addition to a neutralized salt compound formed from a strong acid and a strong base. For example, from a reaction between a commercially available didecyl dimethyl ammonium chloride and adipic acid-sodium obtained from an equimolar reaction between adipic acid and sodium hydroxide, the didecyl dimethyl ammonium adipate which is the antibacterial cationic surfactant of the present invention is produced in addition to sodium chloride. A method for isolating the antibacterial cationic surfactant of the present invention includes column chromatography, a salting-out method utilizing a property that the antibacterial cationic surfactant of the present invention does not dissolve in a high concentration salt solution, and the like.

Although, theoretically, the antibacterial cationic surfactant is preferably neutralized with an acid having an acid dissociation constant higher than the acid dissociation constant (4.26) of acrylic acid; a deodorization effect has also been recognized when neutralization is conducted with an acid having an acid dissociation constant that is slightly lower than the acid dissociation constant of acrylic acid. Specifically, an antibacterial cationic surfactant neutralized with an acid having an acid dissociation constant of 3.0 or more exhibits a deodorization effect. On the other hand, it is difficult to synthesize an antibacterial cationic surfactant neutralized with an acid having an acid dissociation constant of higher than 5.5. Furthermore, the antibacterial cationic surfactant used in the present invention is more preferably neutralized with an acid having an acid dissociation constant that is almost identical to or slightly higher than the acid dissociation constant of acrylic acid. From this standpoint, an acid dissociation constant pKa, in water at 25 degrees centigrade, of an acid used for neutralizing the antibacterial cationic surfactant preferably ranges from 3.00 to 5.50, more preferably from 3.18 to 5.24, and even more preferably from 4.26 to 5.24.

When an acid that dissociates in multiple stages is used, it is preferable that an acid dissociation constant of at least one stage is within a range from 3.0 to 5.5, and it is more preferable that the acid dissociation constants of all the stages are within the range from 3.0 to 5.5. For example, in the case of a compound having the first dissociation acidic group whose acid dissociation constant is beyond the range from 3.0 to 5.5 and the second dissociation acidic group whose acid dissociation constant is within the range from 3.0 to 5.5; it is preferable to cause the first dissociation acidic group whose acid dissociation constant is beyond the range from 3.0 to 5.5 to react with, for example, an alcohol to form an ester, and allow the second dissociation acidic group whose acid dissociation constant is within the range of 3.0 to 5.5 to remain. Specifically, in the case of citric acid, an acid dissociation constant of the first stage is 2.87 and an acid dissociation constant of the second stage is 4.35. In such a case, citric acid monomethyl ester obtained through an equimolar reaction between methanol and the first dissociation acidic functional group of citric acid has a dissociation constant of 4.35 of the remaining acidic group, and can be suitably used in the present invention.

Specific examples of an acid having an acid dissociation constant in water at 25 degrees centigrade in a range from 3.0 to 5.5 include adipic acid (4.26), L-ascorbic acid (4.03), aspartic acid (second stage: 3.7), azelaic acid (4.39), o-anisic acid (4.09), m-anisic acid (4.09), p-anisic acid (4.48), m-aniline sulfonic acid (3.74), p-aniline sulfonic acid (3.23), o-aminobenzoic acid (second stage: 4.95), m-aminobenzoic acid (3.12), p-aminobenzoic acid (second stage: 4.85), 4-aminobutyric acid (4.03), benzoic acid (4.20), isovaleric acid (4.58), isonicotinic acid (second stage: 4.87), methyl isonicotinate (3.26), isobutyric acid (4.63), oxaloacetic acid (second stage: 3.89), octanoic acid (4.89), formic acid (3.55), valeric acid (4.64), quinaldic acid (second stage: 4.75), citric acid (second stage: 4.35), glyoxylic acid (3.18), glycolic acid (3.63), glutamic acid (second stage: 4.20), glutaric acid (4.13), crotonic acid (4.69), m-chlorobenzoic acid (3.82), p-chlorobenzoic acid (3.99), 3-chloropropionic acid (3.92), cinnamic acid (cis) (3.88), cinnamic acid (trans) (4.44), succinic acid (4.00), acetic acid (4.56), m-cyanobenzoic acid (3.60), p-cyanobenzoic acid (3.55), cyclohexane carboxylic acid (4.70), oxalic acid (second stale: 3.82), d-tartaric acid (second stage: 3.95), (R,R)-tartaric acid (second stage: 4.44), 1-naphthoic acid (3.70), 2-naphthoic acid (4.16), m-nitrobenzoic acid (3.45), p-nitrobenzoic acid (3.44), lactic acid (3.66), p-hydroxybenzoic acid (4.58), vinyl acetic acid (4.12), pimelic acid (4.31), 2,6-pyridinedicarboxylic acid (third stage: 4.68), phenylacetic acid (4.10), fumaric acid (second stage: 4.10), o-fluorobenzoic acid (3.27), m-fluorobenzoic acid (3.87), p-fluorobenzoic acid (4.14), propionic acid (4.67), m-bromobenzoic acid (3.81), p-bromobenzoic acid (4.00), hexanoic acid (4.63), heptanoic acid (4.66), o-benzenedicarboxylic acid (second stage: 4.93), m-benzenedicarboxylic acid (3.50), p-benzenedicarboxylic acid (3.54), malonic acid (second stage: 5.28), mandelic acid (3.19), mercaptoacetic acid (3.43), m-iodobenzoic acid (3.85), p-iodobenzoic acid (4.00), butyric acid (4.63), malic acid (3.24), levulinic acid (4.44), etc.

The content of the antibacterial cationic surfactant in 100 mass % of the absorber is preferably 0.0005 mass % or more, more preferably 0.01 mass % or more, and is preferably 0.075 mass % or less, and more preferably 0.050 mass % or less. A sufficient deodorization effect cannot be obtained if the content of the antibacterial cationic surfactant is too low. On the other hand, if the content of the antibacterial cationic surfactant is too high, economic efficiency becomes inferior, and, when it is used for an absorber, return of the body-fluid may be likely to occur.

The absorber of the present invention is not limited, as long as the absorber comprises, as a water-absorbent resin powder, the crosslinked polymer mainly composed of acrylic acid and having carboxyl groups thereof being at least partially neutralized, and the antibacterial cationic surfactant. For example, the absorber of the present invention preferably comprises a liquid-permeable first sheet, a second sheet, and a water absorption layer comprising the water-absorbent resin powder and disposed between the first sheet and the second sheet.

The absorption layer disposed between the first sheet and the second sheet may consist of the water-absorbent resin powder, or may comprise the water-absorbent resin powder and a fibrous base material. It is possible to make the thin absorber, if the water absorption layer consists of the water-absorbent resin powder. The absorber whose water absorption layer comprises the water-absorbent resin powder and the fibrous base material is superior in urine dispersibility.

Examples of the fibrous base material that can be disposed between the first sheet and the second sheet include fiberized pulp, thermal bonding fibers, etc. Examples of the fiberized pulp include pulp fibers known in the art. The thermal bonding fibers are used for enhancing shape-retention. Specific examples of the thermal bonding fibers include fibers of polyolefin such as polyethylene and polypropylene, polyester fibers, and composite fibers.

The first sheet is a sheet that is on the side in contact with skin surface, and allows the body fluid from a wearer to immediately pass therethrough. The liquid-permeable first sheet is preferably a permeable sheet material, e.g., a nonwoven fabric formed from a hydrophilic fiber. Examples of the nonwoven fabric used as the first sheet include point-bond nonwoven fabrics, air-through nonwoven fabrics, spun lace nonwoven fabrics, spunbond nonwoven fabrics, etc. Cellulose, rayon, cotton, etc., can be used as the hydrophilic fiber forming these nonwoven fabrics. It should be noted that, as the first sheet, a liquid-permeable nonwoven fabric formed from a hydrophobic fiber (e.g., polypropylene, polyethylene, polyester, polyamide, nylon) whose surface is hydrophilized with a surfactant may be used.

The second sheet may be either a liquid-permeable sheet or a liquid-non-permeable sheet depending on the usage of the absorber. As the permeable sheet, the same material as the first sheet can be used. As the liquid-non-permeable sheet, a water-repellent or liquid-non-permeable nonwoven fabric (e.g., spunbond nonwoven fabrics, melt-blown nonwoven fabrics, SMS (spunbond-meilblown-spunbond) nonwoven fabrics) formed from a hydrophobic fiber (e.g., polypropylene, polyethylene, polyester, poly amide, nylon), or a water-repellent or liquid-non-permeable plastic film is used. The second sheet prevents the fluid component of excrement that reaches the liquid-non-permeable sheet, from oozing out of the absorber. If a plastic film is used as the liquid-non-permeable sheet, a moisture permeable (air-permeable) plastic film is preferably used from the standpoint that humid feeling is prevented to improve the wear's comfort.

The absorber of the present invention preferably has the antibacterial cationic surfactant applied to at least a part of the water-absorbent resin powder. The deodorization effect becomes high if the antibacterial cationic surfactant exists in or in the vicinity of the water-absorbent resin powder. Specifically, the antibacterial cationic surfactant is preferably applied to the upper part (on the first sheet side) of the water absorption layer.

In the following, the absorber and the absorbent article of the present invention will be described with reference to the drawings; however, the present invention is not limited to embodiments shown in the drawings. FIG. 1 is a schematic sectional view of a preferable embodiment of the absorber of the present invention. The absorber 1 of the present invention comprises a liquid-permeable first sheet 2, a second sheet 3, and a water absorption layer consisting of the water-absorbent resin powder 4 and disposed between the first sheet 2 and the second sheet 3. The water-absorbent resin powder 4 is adhered to the first sheet 2 and the second sheet 3 using, for example, a hot-melt adhesive (not shown). FIG. 2 is a schematic sectional view of another preferable embodiment of the absorber of the present invention. In this embodiment, the first sheet 2 and the second sheet 3 are attached to each other at a predetermined interval to provide water-absorbent resin powder absent regions 5a where the water-absorbent resin powder does not exist and water-absorbent resin powder present regions 5b where the water-absorbent resin powder is enveloped by the first sheet and the second sheet. When another absorber is further provided in a lower layer for the absorber of this embodiment, the water-absorbent resin powder absent regions 5a become passages for body fluid, and the body fluid can easily pass therethrough to reach the lower layer. FIG. 3 is a schematic sectional view of another preferable embodiment of the absorber of the present invention. This absorber includes the liquid-permeable first sheet 2, the second sheet 3, and a water absorption layer including the water-absorbent resin powder 4 and a fibrous base material 6 disposed between the first sheet 2 and the second sheet 3.

In the embodiments shown in FIGS. 1 to 3, for example, the antibacterial cationic surfactant is preferably applied to the upper part of the water absorption layer on the inner side of the first sheet. By directly applying the antibacterial cationic surfactant to the water absorption layer, the deodorization effect is enhanced.

FIG. 4 is a schematic sectional view showing a preferable embodiment of the absorbent article of the present invention. The absorbent article 9 comprises a liquid-permeable top sheet 10, a liquid-non-permeable back sheet 11, and an absorber 1a and an absorber 1b laminated into two layers between the top sheet 10 and the back sheet 11. The liquid-non-permeable side sheets 12 are jointed to upper portions of both side-edge portions of the top sheet 10. The portions of the side sheets 12 inward of joint points 13 form rise-flaps which are to rise toward the wearer's skin. The absorber 1a of the present invention includes a first sheet 2, a second sheet 3, and a water absorption layer consisting of the water-absorbent resin powder 4 and disposed between the first sheet 2 and the second sheet 3. The absorber 1b includes a first sheet 2, a second sheet 3, and a water absorption layer comprising the water-absorbent resin powder 4 and the fibrous base material 6 and disposed between the first sheet 2 and the second sheet 3. In the absorbent article of this embodiment, at least one of the absorber 1a and the absorber 1b preferably comprises the antibacterial cationic surfactant; and more preferably, both the absorber 1a and the absorber 1b comprise the antibacterial cationic surfactant. It should be noted that the absorber may be formed of a single layer.

The present invention includes an absorbent article provided with the absorber of the present invention. Specific examples of the absorbent article include disposable diapers, sanitary napkins, incontinence pads, breast-milk pads, absorbent articles for pets, etc.

EXAMPLES

In the following, the present invention will be described in detail by means of Examples. However, the present invention is not limited to the following Examples, and changes and embodiments that do not depart from the essence of the present invention are also included in the scope of the present invention.

(Manufacturing an Absorber)

Cationic surfactants shown in Table 1 were applied to a surface of a water absorption layer including, as a water-absorbent resin powder, a crosslinked polymer main composed of acrylic acid and having carboxyl groups being at least partially neutralized. This absorption layer was sandwiched between a first sheet which is a liquid-permeable top sheet and a second sheet which is a polyethylene-film back sheet to manufacture an assembly-type absorber that is to be worn at the waist portion by fixing with a pressure sensitive adhesive tape.

TABLE 1

| Absorber | Type of SAP | Antibacterial cationic surfactant Compound name | pKa of Acid | Content (%) | Deodorizability evaluation |
|---|---|---|---|---|---|
| Example 1 | SAP1 | Mono (dodecyl monobenzyl dimethyl ammonium) adipate | 4.26 | 0.001 | 2.4 |
| Example 2 | SAP1 | Mono (dodecyl monobenzyl dimethyl ammonium) adipate | 4.26 | 0.010 | 2.3 |
| Example 3 | SAP1 | Mono (dodecyl monobenzyl dimethyl ammonium) adipate | 4.26 | 0.050 | 2.3 |
| Example 4 | SAP1 | Mono (tetradecyl monobenzyl dimethyl ammonium) adipate | 4.26 | 0.010 | 2.6 |
| Example 5 | SAP1 | Mono (dodecyl monobenzyl dimethyl ammonium) succinate | 4.0 | 0.010 | 2.5 |
| Example 6 | SAP1 | Mono (dodecyl monobenzyl dimethyl ammonium) citric acid acetate salt | 4.35 | 0.010 | 3.4 |
| Example 7 | SAP1 | Mono (dodecyl monobenzyl dimethyl ammonium) succinic acid acetate salt | 5.24 | 0.010 | 3.3 |
| Example 8 | SAP1 | Mono (dodecyl monobenzyl dimethyl ammonium) glyoxylic acid salt | 3.18 | 0.010 | 2.9 |
| Example 9 | SAP1 | Mono (tetradecyl trimethyl ammonium) adipate | 4.26 | 0.010 | 2.3 |
| Example 10 | SAP1 | Mono (didecyl dimethyl ammonium) adipate | 4.26 | 0.010 | 2.0 |
| Example 11 | SAP1 | Mono (tetradecyl pyridinium) adipate | 4.26 | 0.010 | 2.2 |
| Example 12 | SAP2 | Mono (dodecyl monobenzyl dimethyl ammonium) adipate | 4.26 | 0.010 | 2.4 |
| Comparative Example 1 | — | none | — | — | 4.7 |
| Comparative Example 2 | SAP1 | Mono (dodecyl monobenzyl dimethyl ammonium) citrate | 2.87 | 0.010 | 4.2 |
| Comparative Example 3 | SAP1 | Mono (tetradecyl monobenzyl dimethyl ammonium) citrate | 2.87 | 0.010 | 4.3 |
| Comparative Example 4 | SAP1 | Mono (tetradecyl trimethyl ammonium) citrate | 2.87 | 0.010 | 4.2 |
| Comparative Example 5 | SAP1 | Mono (didecyl dimethyl ammonium) citrate | 2.87 | 0.010 | 4.1 |
| Comparative Example 6 | SAP1 | Mono (tetradecyl pyridinium) citrate | 2.87 | 0.010 | 4.2 |
| Comparative Example 7 | SAP1 | (Dodecyl monobenzyl dimethyl ammonium) chloride salt | −8 | 0.010 | 4.6 |

SAP1: A water-absorbent resin powder obtained by partially neutralizing carboxyl groups of a crosslinked polymer mainly composed of acrylic acid with a sodium ion: SANWET IM-930 (San-Dia Polymers, Ltd.).
SAP2: A water-absorbent resin powder obtained by partially neutralizing carboxyl groups of a crosslinked polymer mainly composed of acrylic acid with a sodium ion: Aqua Keep SA60S (Sumitomo Seika Chemicals Co., Ltd.).

(Evaluation of Deodorizability)

The absorbers obtained in the Examples and Comparative Examples were worn for 4 hours by 20 adult urine subjects, and were then removed. When removing absorbers, a sensory test for the presence or absence of an odor was performed, and a six-point scale evaluation was conducted based on an <Evaluation Standard>. Average values of the points are also shown in Table 1.

<Evaluation Standard>
5 points: Intense odor
4 points: Strong odor
3 points: Easily detectable odor
2 points: Source-identifiable weak odor
1 point: Barely detectable odor
0 points: Odorless From a comparison between Examples 1 to 11 and Comparative Examples 1 to 7, it can be understood that excellent deodorization effect is obtained by the absorber of the present invention using, as an antibacterial cationic surfactant, a compound neutralized with an acid having an acid dissociation constant pKa in water at 25 degrees centigrade in a range from 3.0 to 5.5.

The present invention includes the following embodiments.

Embodiment 1

An absorber comprising, a crosslinked polymer mainly composed of acrylic acid and having carboxyl groups thereof being at least partially neutralized as a water-absorbent resin powder, and an antibacterial cationic surfactant, wherein the antibacterial cationic surfactant is a compound neutralized with an acid having an acid dissociation constant pKa in water at 25 degrees centigrade in a range from 3.0 to 5.5.

Embodiment 2

The absorber according to embodiment 1, wherein the antibacterial cationic surfactant is applied to at least a part of the water-absorbent resin powder.

Embodiment 3

The absorber according to embodiment 1 or 2, wherein the absorber comprises the antibacterial cationic surfactant in a content from 0.0005 mass % to 0.050 mass %.

Embodiment 4

The absorber according to any one of embodiments 1 to 3, wherein the antibacterial cationic surfactant is a compound neutralized with an acid having an acid dissociation constant pKa in water at 25 degrees centigrade in a range from 3.18 to 5.24.

Embodiment 5

The absorber according to any one of embodiments 1 to 4, wherein the antibacterial cationic surfactant is at least one compound selected from the group consisting of monoalkyl trimethyl ammonium salts, dialkyl dimethyl ammonium salts, monoalkyl monobenzyl dimethyl ammonium salts, and monoalkyl pyridinium salts.

Embodiment 6

The absorber according to any one of embodiments 1 to 5, wherein the carboxyl groups of the crosslinked polymer are at least partially neutralized with a sodium ion.

Embodiment 7

The absorber according to any one of embodiments 1 to 6, further comprising a liquid-permeable first sheet, a second sheet, and an absorption layer comprising the water-absorbent resin powder disposed between the first sheet and the second sheet.

Embodiment 8

An absorbent article comprising the absorber according to any one of embodiments 1 to 7.

INDUSTRIAL APPLICABILITY

The present invention can be suitably used for deodorization of, for example, absorbent articles such as incontinence pads, disposable diapers, sanitary napkins, breast-milk pads, and absorbent articles for pets, and absorbers used in absorbent articles.

REFERENCE SIGNS LIST

1: absorber, 2: first sheet, 3: second sheet, 4: water-absorbent resin powder, 5*a*: water-absorbent resin absent region, 5*b*: water-absorbent resin presence region, 6: fibrous base material, 7: water-absorbent resin powder, 9: absorbent article, 10: top sheet, 11: back sheet, 12: side sheet, 13: joint point, 14: elastic member

The invention claimed is:

1. An absorber comprising a water-absorbent resin powder and an antibacterial cationic surfactant,
   wherein the water-absorbent resin powder is a crosslinked polymer composed of 90 mass % or more of acrylic acid and having carboxyl groups thereof being at least partially neutralized, and
   wherein the antibacterial cationic surfactant is at least one member selected from the group consisting of a quaternary ammonium adipate, a quaternary ammonium succinate, and a quaternary ammonium glyoxylate.

2. The absorber according to claim 1, wherein the antibacterial cationic surfactant is applied to at least a part of the water-absorbent resin powder.

3. The absorber according to claim 1, wherein the absorber comprises the antibacterial cationic surfactant in a content from 0.0005 mass % to 0.050 mass %.

4. The absorber according to claim 1, wherein the carboxyl groups of the crosslinked polymer are at least partially neutralized with a sodium ion.

5. The absorber according to claim 1, comprising a liquid-permeable first sheet, a second sheet, and an absorption layer comprising the water-absorbent resin powder and disposed between the first sheet and the second sheet.

6. The absorber according to claim 1, wherein the quaternary ammonioum moiety of the antibacterial cationic surfactant is at least one member selected from the group consisting of monoalkyl trimethyl ammonium, dialkyl dimethyl ammonium, monoalkyl monobenzyl dimethyl ammonium, and monoalkyl pyridinium.

7. An absorbent article comprising an absorber, wherein the absorber comprises a water-absorbent resin powder and an antibacterial cationic surfactant,
   wherein the water-absorbent resin powder is a crosslinked polymer composed of 90 mass % or more of acrylic acid and having carboxyl groups thereof being at least partially neutralized, and
   wherein the antibacterial cationic surfactant is at least one member selected from the group consisting of a quaternary ammonium adipate, a quaternary ammonium succinate, and a quaternary ammonium glyoxylate.

8. The absorbent article according to claim 7, wherein the antibacterial cationic surfactant is applied to at least a part of the water-absorbent resin powder.

9. The absorbent article according to claim 7, wherein the absorber comprises the antibacterial cationic surfactant in a content from 0.0005 mass % to 0.050 mass %.

10. The absorbent article according to claim 7, wherein the carboxyl groups of the crosslinked polymer are at least partially neutralized with a sodium ion.

11. The absorbent article according to claim 7, wherein the absorber comprises a liquid-permeable first sheet, a second sheet, and an absorption layer comprising the water-absorbent resin powder and disposed between the first sheet and the second sheet.

12. The article according to claim 7, wherein the quaternary ammonioum moiety of the antibacterial cationic surfactant is at least one member selected from the group consisting of monoalkyl trimethyl ammonium, dialkyl dimethyl ammonium, monoalkyl monobenzyl dimethyl ammonium, and monoalkyl pyridinium.

\* \* \* \* \*